(12) United States Patent
Sigurdsson

(10) Patent No.: US 11,850,257 B2
(45) Date of Patent: Dec. 26, 2023

(54) METHOD FOR ENHANCING BETA-ADRENERGIC RESPONSE

(71) Applicant: Saganatura EHF., Hafnarfjördur (IS)

(72) Inventor: Steinthor Sigurdsson, Reykjavik (IS)

(73) Assignee: SAGANATURA EHF., Hafnarfjordur (IS)

(*) Notice: Subject to any disclaimer, the term of this patent is extended or adjusted under 35 U.S.C. 154(b) by 0 days.

(21) Appl. No.: 17/429,695

(22) PCT Filed: Feb. 11, 2020

(86) PCT No.: PCT/IS2020/050001
§ 371 (c)(1),
(2) Date: Aug. 10, 2021

(87) PCT Pub. No.: WO2020/165925
PCT Pub. Date: Aug. 20, 2020

(65) Prior Publication Data
US 2022/0202840 A1    Jun. 30, 2022

(30) Foreign Application Priority Data
Feb. 11, 2019 (IS) .......................................... EU9111

(51) Int. Cl.
| A61K 31/7048 | (2006.01) |
| A61P 13/10 | (2006.01) |
| A61K 9/48 | (2006.01) |
| A61K 36/232 | (2006.01) |
| A61K 36/234 | (2006.01) |
| A61K 36/505 | (2006.01) |

(52) U.S. Cl.
CPC .......... A61K 31/7048 (2013.01); A61K 9/48 (2013.01); A61K 36/232 (2013.01); A61K 36/234 (2013.01); A61K 36/505 (2013.01); A61P 13/10 (2018.01)

(58) Field of Classification Search
None
See application file for complete search history.

(56) References Cited

U.S. PATENT DOCUMENTS

2013/0172277 A1    7/2013    Caltabiano

FOREIGN PATENT DOCUMENTS

| CN | 106692666 A | 5/2017 |
| CN | 109091524 A | 12/2018 |
| WO | 2005056544 A1 | 6/2005 |
| WO | WO-2005123063 A1 * | 12/2005 ........... A23L 33/105 |
| WO | 2017164707 A1 | 9/2017 |

OTHER PUBLICATIONS

Kim, S.B., et al., Anti-adipogenic chromosome glycosides from Cnidium monnieri fruits in 3T3-L1 cells, Bioorganic & Medicinal Chem Letters 22 (2012) 6267-6271 (Year: 2012).*
Duan, Y-D., et al., The antitumor activity of naturally occurring chromones: A review, Fitoteropia 135 (2019) 114-129 (Year: 2019).*
Baba, K., Chromonoe glucosides from Cnidium Japonicum, Phytochemistry, 35 (1994) 221-224 (Year: 1994).*
Sigurdsson, S., et al., A parallel, randomized, double-blind, placebo-controlled study to investigate the effect of SagaPro on nocturia in men, Scandinavian Journal of Urology, 2013; 47: 26-32 (Year: 2013).*
International Search Report and Written Opinion dated May 14, 2020 for corresponding International Application No. PCT/IS2020/050001.
Kim, Seon Beom et al. "Anti-adipogenic chromone glycosides from Cnidium monnieri fruits in 3T3-L1 cells." Bioorganic & medicinal chemistry letters vol. 22, 19 (2012): 6267-71. doi:10.1016/j.bmcl.2012.07.103.
Duan, Ya-Di et al. "The antitumor activity of naturally occurring chromones: A review." Fitoterapia vol. 135 (2019): 114-129. doi:10.1016/j.fitote.2019.04.012.
Kitajima, J. et al. (1999). Monoterpenoid Glucosides of Cnidium monnieri Fruit. Chemical & Pharmaceutical Bulletin, vol. 47, No. 5, 639-642. doi:10.1248/cpb.47.639.
Baba, K. et al. (1993). Chromone glucosides from Cnidium japonicum. Phytochemistry, vol. 35, No. 1, 221-225. doi:10.1016/s0031-9422(00)90538-7.
Sigurdsson, S., et al. (2012). A parallel, randomized, double-blind, placebo-controlled study to investigate the effect of SagaPro on nocturia in men. Scandinavian Journal of Urology, 47(1), 26-32. doi:10.3109/00365599.2012.69539.
Kowal, N.M. et al.: "Investigations on the constituents of SagaPro tablets, a food supplement manufactured from Angelica archangelica leaf", Die Pharmazie—An International Journal of Pharmaceutical Sciences, vol. 72, No. 1 (2017), pp. 3-4, DOI: https://doi.org/10.1691/ph.2017.6807.

* cited by examiner

Primary Examiner — H. Sarah Park
(74) Attorney, Agent, or Firm — TAROLLI, SUNDHEIM, COVELL & TUMMINO L.L.P.

(57) ABSTRACT

The present invention provides cnidimoside A for use in the treatment of urinary conditions such as overactive bladder and related syndromes. The invention also relates to methods of treatment of overactive bladder using cnidimoside A. The compound can be administered purified or as a plant extract.

7 Claims, 2 Drawing Sheets

METHOD FOR ENHANCING BETA-ADRENERGIC RESPONSE

RELATED APPLICATIONS

The present application is a U.S. National Stage application under 35 USC 371 of PCT Application Serial No. PCT/IS2020/050001, filed on 11 Feb. 2020; which claims priority from IS Patent Application No. EU9111, filed 11 Feb. 2019, the entirety of both of which are incorporated herein by reference.

FIELD

The invention is within the field of treatment of urinary conditions, such as overactive bladder, nocturia and urinary incontinence, and compounds for use thereof.

BACKGROUND

Cnidimoside A (5,7-dihydroxy-2-methyl-6-[(Z)-3-methyl-4-[(2R,3R,4S,5S,6R)-3,4,5-trihydroxy-6-(hydroxymethyl)oxan-2-yl]oxybut-2-enyl]chromen-4-one) is a chromone known to occur in plants of the genus Cnidium (Phytochemistry, Vol. 35, No. 1, December 1993, pp. 221-225, Fitoterapia Vol. 82, No. 5, July 2011, pp. 767-771). It has been shown to have antitumour properties (J. Nat. Med. Vol. 62, No. 3, July 2008, pp. 308-313), and anti-adipogenic properties (Bioorg. Med. Chem. Lett., Vol. 22, No. 19, October 2012, pp. 6267-6271).

Cnidimoside A

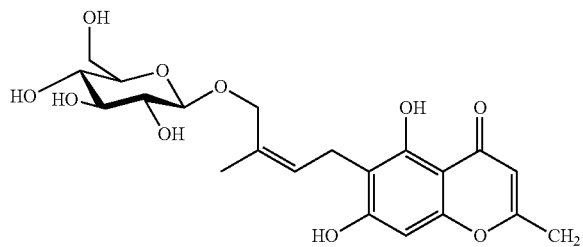

Overactive bladder (OAB) is defined as a symptom complex comprising urinary urgency, with or without urgency incontinence (urinary incontinence), urinary frequency and nocturia (waking up one or more times at night to urinate), in the absence of other local or metabolic factors that would account for the symptoms (Maturitas, Vol. 66, No. 3, July 2010, pp. 257-262). Overactive bladder can lead to a significant negative effect on a person's life, and is a major source of urinary incontinence. The condition, while not life threatening, can affect individuals for years.

The causes of OAB are poorly understood at present (Maturitas, Vol. 66, No. 3, July 2010, pp. 257-262). Acetylcholine and noradrenaline are important neurotransmitters in the control of detrusor (bladder muscle) activity, the former signalling contraction via muscarinic receptors, and the latter signalling relaxation via β-adrenergic receptors (βARs).

Current management options of overactive bladder syndromes include lifestyle changes and medication. Lifestyle changes include fluid restriction, avoidance of caffeine, bladder retraining and pelvic exercises. These have however limited benefit. A number of drugs have been used for treatment of overactive bladder, including antimuscarinic drugs and β3 adrenergic receptor agonists. Few individuals however appear to obtain complete relief from these medications, side effects are considerable and long-term compliance is a concern.

There is accordingly a need for improved medical intervention to treat overactive bladder syndromes.

SUMMARY

The present invention discloses a method for enhancing β-adrenergic response by administering cnidimoside A to treat a condition in which enhancement of β-adrenergic response is desirable. It is demonstrated herein that cnidimoside A enhances β-adrenergic response by repressing desensitization of β-adrenergic receptors, thus counteracting diminished response.

The present invention further discloses a method for enhancing β-adrenergic response by administering cnidimoside A to treat a condition in which enhancement of β-adrenergic response is desirable.

In an aspect, the invention relates to cnidimoside A (5,7-dihydroxy-2-methyl-6-[(Z)-3-methyl-4-[(2R,3R,4S,5S,6R)-3,4,5-trihydroxy-6-(hydroxymethyl)oxan-2-yl]oxybut-2-enyl]chromen-4-one) for use in a method of treatment of a urinary condition.

In another aspect, the invention relates to a method of treatment of a urinary condition in a human subject, the method comprising administering to a human subject in need thereof a therapeutically active dose of cnidimoside A.

In another aspect, the invention relates to a pharmaceutical composition comprising cnidimoside A and one or more pharmaceutically acceptable excipients, for use in the treatment of a urinary condition in a human individual.

Yet another aspect of the invention relates to an extract from a plant from the genus Cnidium, Angelica or Corydalis, the extract comprising 0.2 to 20 mg cnidimoside A for each gram of the plant material (total plant extract), for use in the treatment of a urinary condition.

The urinary condition can be overactive bladder, or be manifested as an overactive bladder. In some embodiments, the urinary condition is selected from overactive bladder, nocturia and urinary incontinence.

Cnidimoside A can be provided in a pure or purified form, e.g. as a compound purified from a suitable source, e.g. plants. Cnidimoside A can also, or alternatively, be provided as a plant extract from one or more plant, as further described herein.

When in a pure or purified form, cnidimoside A can have a purity of 80% or more, 85% or more, 90% or more, 95% or more, 96% or more, 97% or more, 98% or more, or 99% or more.

The above features along with additional details of the invention, are described further in the description and examples below, which are intended to further illustrate the invention but are not intended to limit its scope in any way.

BRIEF DESCRIPTION OF THE DRAWINGS

The skilled person will understand that the drawings, described below, are for illustration purposes only. The drawings are not intended to limit the scope of the present teaching in any way.

Figure 2:
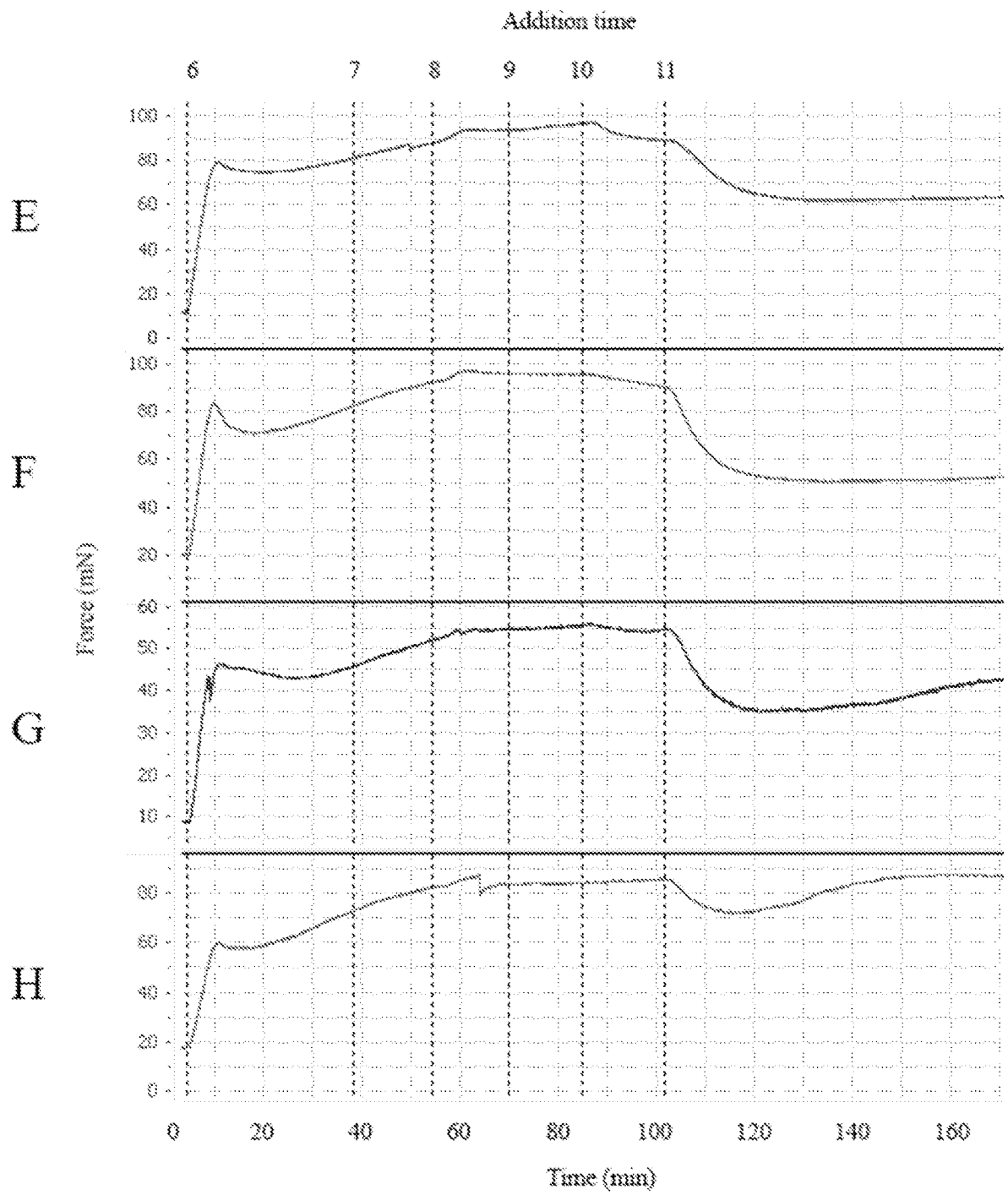

FIG. 2 shows the recorded contractions in four muscle strips in organ baths in Experiment II. All muscle strips are contracted by potassium. At time 7-10 the concentration of cnidimoside A is gradually increased to 200 µM in the top 3 baths, the muscle strip in the bottom bath being control. At time 11 adrenaline is added to each bath to a concentration of 2 µM.

DESCRIPTION

The present invention is based on the observation that cnidimoside A has a relaxing effect on bladder, as shown by experiments performed in an animal model, using bladders from pig (see Example 1 herein). Without intending to be limited by theory, the biological effects of cnidimoside A are believed to at least partially be manifested through the effects of the compound on the β-adrenergic response in bladder, i.e. through the suppression of desensitization of β-adrenergic receptors.

β-adrenergic receptors are activated by the natural agonists epinephrine (adrenaline) and norepinephrine (noradrenaline). They are abundant in the heart, in smooth muscle and in fat tissue. There are three main subgroups of the receptors, β1 being most prominent in the heart but β2 being present there as well. β2 is most abundant in vessel cell smooth muscle, and bronchial tracts, and β3 in detrusor muscle (where (β2 is also present) and fat tissue. Thus β agonists are used as medication for a number of symptoms such as to treat angina (β1 agonists), to cause dilation of bronchial passages, vasodilation in muscle and liver (β2 agonists), and relax detrusor, such as in the treatment of the symptoms of overactive bladder (β3 agonists).

It is demonstrated herein that cnidimoside A enhances β-adrenergic response by repressing desensitization of β-adrenergic receptors in porcine detrusors, where both β2 and β3-receptors are present, thus counteracting diminished response. Thus, the compound has an effect comparable to β-adrenergic agonists acting on either or both of β2 and β3 adrenergic receptors.

The present invention provides to a method for treating conditions in which enhancement of β-adrenergic response is desirable, by administering cnidimoside A, a known component of *Cnidium japonicum* and *Cnidium monnieri*. The present inventors have concluded based on chemical analysis that cnidimoside A is also present in leaves of *Angelica archangelica*. The compound has also been found in the unrelated genus *Corydalis* (Food & Function, Vol. 7, No. 12, December 2016, pp. 4823-4829). As a consequence, cnidimoside A is likely found in species of the genus *Cnidium*, the genus *Angelica* and the genus *Corydalis*.

Cnidimoside A can be obtained in a pure or purified format, i.e. as a pure or purified compound, for example as a compound purified from a plant of the genus *Cnidium*, the genus *Angelica* or the genus *Corydalis*. The compound can for example be obtained in a pure or purified format from *Angelica archangelica*.

Cnidimoside A is not known to have any toxic effects, as also supported by the results shown in Example 3 herein. The dried leaf of *Angelica archangelica* contains on average 2 mg cnidimoside A per gram plant material. The British herbal Pharmacopoeia recommends infusion of up to 15 g *Angelica archangelica* leaf daily (British herbal pharmacopoeia, British herbal medicines association, 1983, pp. 25-26). As cnidimoside A is highly water soluble this dose would lead to up to 30 mg cnidimoside A daily.

Plant extracts useful in the invention can in general be any plant extract comprising cnidimoside A. Exemplary plant extracts include plant extracts from one or more plant from a genus selected from *Cnidium, Angelica* and *Corydalis*. Accordingly, cnidimoside A can be administered as a plant extract, for example as an extract of a plant from the genus *Cnidium*, a plant from the genus *Angelica* (e.g., an extract from *Angelica archangelica*) or a plant from the genus *Corydalis*. The compound can also be provided as a mixture of such extracts.

Plant extracts to be used in the methods described herein can in general comprise cnidimoside A in an amount that is at least 0.1 mg cnidimoside A per each gram plant material (i.e. the total extracted plant material, dry weight), such as at least 0.2 mg, 0.5 mg, or at least 1.0 mg per each gram plant material. The plant extract can comprise as high as 100 mg cnidimoside A per each gram plant material, as high as 50 mg cnidimoside A per each gram plant material, as high as 30 mg cnidimoside A per each gram plant material, or as high as 20 mg cnidimoside A per each gram plant material. The plant extracts can comprise in the range of 0.2 to 30 mg cnidimoside A per gram plant material, in the range of 0.2 to 20 mg cnidimoside A per gram plant material, preferably in the range of 0.5 to 15 mg per gram plant material, even more preferably in the range of 1.0 to 10 mg per gram plant material, such as in the range of 1.0 to 5 mg per gram plant material.

Plant extracts can be prepared using methods known in the art, e.g. through extraction using warm or hot water. Such extracts can subsequently be dried to provide a dry plant extract comprising cnidimoside A.

Biological studies of the bladder have included use of muscle strips and isolated cells from bladder. Whole-bladder studies of pig bladder have also been reported and rodent models to study overactive bladder have been developed (Br J Pharmacol. 171(4):995-1006). Overall, reported studies have shown that animal models can provide valuable insights into the biological mechanisms of the bladder and can be useful in clinical studies of overactive bladder.

Acetylcholine and noradrenaline are important neurotransmitters in the control of detrusor activity, the former signalling contraction via muscarinic receptors, and the latter signalling relaxation via β-adrenergic receptors (βARs). Thus the main oral treatments for symptomatic treatment of OAB are applying muscarinic receptor antagonists to reduce contraction and applying βAR agonists to promote relaxation (Investig. Clin. Urol., Vol. 58, No. 4, July 2017, pp. 261-266). βARs are subject to desensitization upon exposure to agonists, thus reducing their sensitivity to the agonist, leading to a weaker response (Cell Signal, Vol. 38, October 2017, pp. 127-133).

Thus, the main oral treatments for symptomatic treatment of OAB are applying muscarinic receptor antagonists to reduce contraction and applying βAR agonists to promote relaxation (Investig. Clin. Urol., Vol. 58, No. 4, July 2017, pp. 261-266). Nocturia is defined as the complaint that the individual has to wake up at night one or more times for voiding (i.e. to urinate) (Eur. Urol., Vol. 62, No. 5, July 2012, pp. 877-890). The underlying causes of nocturia are varied, and often unknown, but OAB is among them (Eur. Urol., Vol. 62, No. 5, July 2012, pp. 877-890). βARs are subject to desensitization upon exposure to agonists, thus reducing their sensitivity to the agonist, leading to a weaker response (Cell Signal, Vol. 38, October 2017, pp. 127-133).

It is believed that compounds that enhance β-adrenergic response by reducing desensitization have an effect to similar to β-adrenergic agonists. The proposed mechanism of cnidimoside A can therefore explain the observed effects of the compound in biological studies (see Examples).

Pharmaceutical compositions comprising cnidimoside A can be formulated for non-invasive or invasive delivery. For example, the compositions may be formulated for oral, topical, transmucosal, vaginal, ocular, rectal or inhalation delivery. The compositions may also, or alternatively, be formulated for injection. The compositions may further be formulated for immediate or sustained delivery.

Pharmaceutical compositions for oral delivery can in general be provided as tablets or capsules. The tablets or capsules can comprise pure or purified cnidimoside A, or they can comprise a plant extract comprising cnidimoside A.

Individual doses of cnidimoside A having therapeutic activity can generally be in the range of 0.01 to 100 mg per day. Preferably, the daily dosage can be in the range of 0.05 to 50 mg per day, in the range of 0.1 to 50 mg per day, in the range of 0.1 to 10 mg per day or in the range of 0.1 to 5 mg per day.

Plant extracts useful in the methods can comprise use of plant leaf in the range of 5 to 5000 mg daily, such as in the range of 10 to 1000 mg daily, such as in the range of 50 to 500 mg daily, such as in the range of 100 to 300 mg daily.

An exemplary embodiment comprises an oral tablet containing in the range of 0.1 to 5 mg of cnidimoside, such as in the range of 0.1 to 1 mg of cnidimoside A, such as in the range of 0.1 to 0.5 mg of cnidimoside A, purified or in an herbal or plant extract, for daily consumption of one or more tablet.

In another exemplary embodiment, cnidimoside A is provided as an oral tablet containing 10-1000 mg of dried plant extract obtained from plant leaves, such as 20-500 mg of dried plant extract, such as 50-200 mg of dried plant extract, such as 100-200 mg of dried plant extract, e.g. plant extract from the leaf of *Angelica archangelica*. In the range of 0.1 to 5 mg, such as 0.1 to 1 mg, or 0.1 to 0.5 mg of the plant extract in the tablet can be cnidimoside A. The extract is preferably obtained by aqueous extraction of plant material and the aqueous extract subsequently dried to provide a dry plant extract for oral administration.

The daily dosage can be provided as a single dose. Alternatively, the daily dosage can be provided in two, three or more daily doses that are preferably equal. For example, a daily dose of 10 mg cnidimoside A can be provided as two doses of 5 mg each or as a single dose of 10 mg. It will be appreciated that doses of plant extracts comprising cnidimoside A can also be provided once daily or in two or more daily doses that preferably equal.

Pharmaceutical compositions comprising cnidimoside A, including plant extracts, may comprise one or more pharmaceutically acceptable carrier, excipient or diluent.

Pharmaceutical excipients are known in the art, and generally serve the role of providing the resulting composition with increased long-term stability, facilitate adsorption, enhance solubility, providing flowability or non-stick properties and also prevent degradation or aggregation over time.

Exemplary excipients include fillers, binders, disintegrants, coatings, sorbents, antiadherents, lubricants, glidants, preservatives, antioxidants, flavouring agents, sweeteners, colouring agents, solvents, buffering agents, chelating agents, viscosity imparting agents, surface active agents and humectants.

The diluents, excipients or carriers that may be used are well known in the formulation art and the form chosen for any particular regimen will depend on the given context and the formulator's choice.

Cnidimoside A, including pharmaceutical formulations comprising cnidimoside A, can be administered concurrently with one or more additional pharmaceutically active ingredient, for example pharmaceutically active compounds for treating urinary conditions such as overactive bladder. Examples of such compounds includes antimuscarinic drugs (e.g., darifenacin, hyoscyamine, oxybutynin, tolterodine, solifenacin, trospium, fesoterodine) and β3 adrenergic receptor agonists (e.g. mirabegron).

As used herein, including in the claims, singular forms of terms are to be construed as also including the plural form and vice versa, unless the context indicates otherwise. Thus, it should be noted that as used herein, the singular forms "a," "an," and "the" include plural references unless the context clearly dictates otherwise.

Throughout the description and claims, the terms "comprise", "including", "having", and "contain" and their variations should be understood as meaning "including but not limited to", and are not intended to exclude other components.

The present invention also covers the exact terms, features, values and ranges etc. in case these terms, features, values and ranges etc. are used in conjunction with terms such as about, around, generally, substantially, essentially, at least etc. (i.e., "about 3" shall also cover exactly 3 or "substantially constant" shall also cover exactly constant).

The term "at least one" should be understood as meaning "one or more", and therefore includes both embodiments that include one or multiple components. Furthermore, dependent claims that refer to independent claims that describe features with "at least one" have the same meaning, both when the feature is referred to as "the" and "the at least one".

It will be appreciated that variations to the foregoing embodiments of the invention can be made while still falling within the scope of the invention can be made while still falling within scope of the invention. Features disclosed in the specification, unless stated otherwise, can be replaced by alternative features serving the same, equivalent or similar purpose. Thus, unless stated otherwise, each feature disclosed represents one example of a generic series of equivalent or similar features.

Use of exemplary language, such as "for instance", "such as", "for example" and the like, is merely intended to better illustrate the invention and does not indicate a limitation on the scope of the invention unless so claimed. Any steps described in the specification may be performed in any order or simultaneously, unless the context clearly indicates otherwise.

All of the features and/or steps disclosed in the specification can be combined in any combination, except for combinations where at least some of the features and/or steps are mutually exclusive. In particular, preferred features of the invention are applicable to all aspects of the invention and may be used in any combination.

The invention is further described in the following non-limiting examples.

Example 1

Bladders were obtained from freshly slaughtered pigs and placed in cold Krebs solution (composition, mM: sodium chloride 119, potassium chloride 4.6, sodium bicarbonate 15, calcium chloride 1.5, magnesium chloride 1.2, sodium dihydrogen phosphate 1.2, glucose was 1.98 g/L) which had been gassed by 5% $CO_2$ and put on ice. Subsequently four adjacent strips were cut from the detrusor (typically 2 mm wide and 20 mm long). In each case, four strips were cut, one of which served as a control. The tissues were mounted in a 100-mL organ bath containing sodium Krebs solution, which was maintained at 37° C. and continuously gassed with 95% O2 and 5% CO2. The strips were placed under a tension of ≈1 g and allowed to equilibrate for 60 minutes, during which the bath was changed three times. The muscle contraction was recorded by a transducer. The muscle strips were then contracted by addition of potassium up to 50 mM and allowed to equilibrate.

Experiment I

Figure 1:
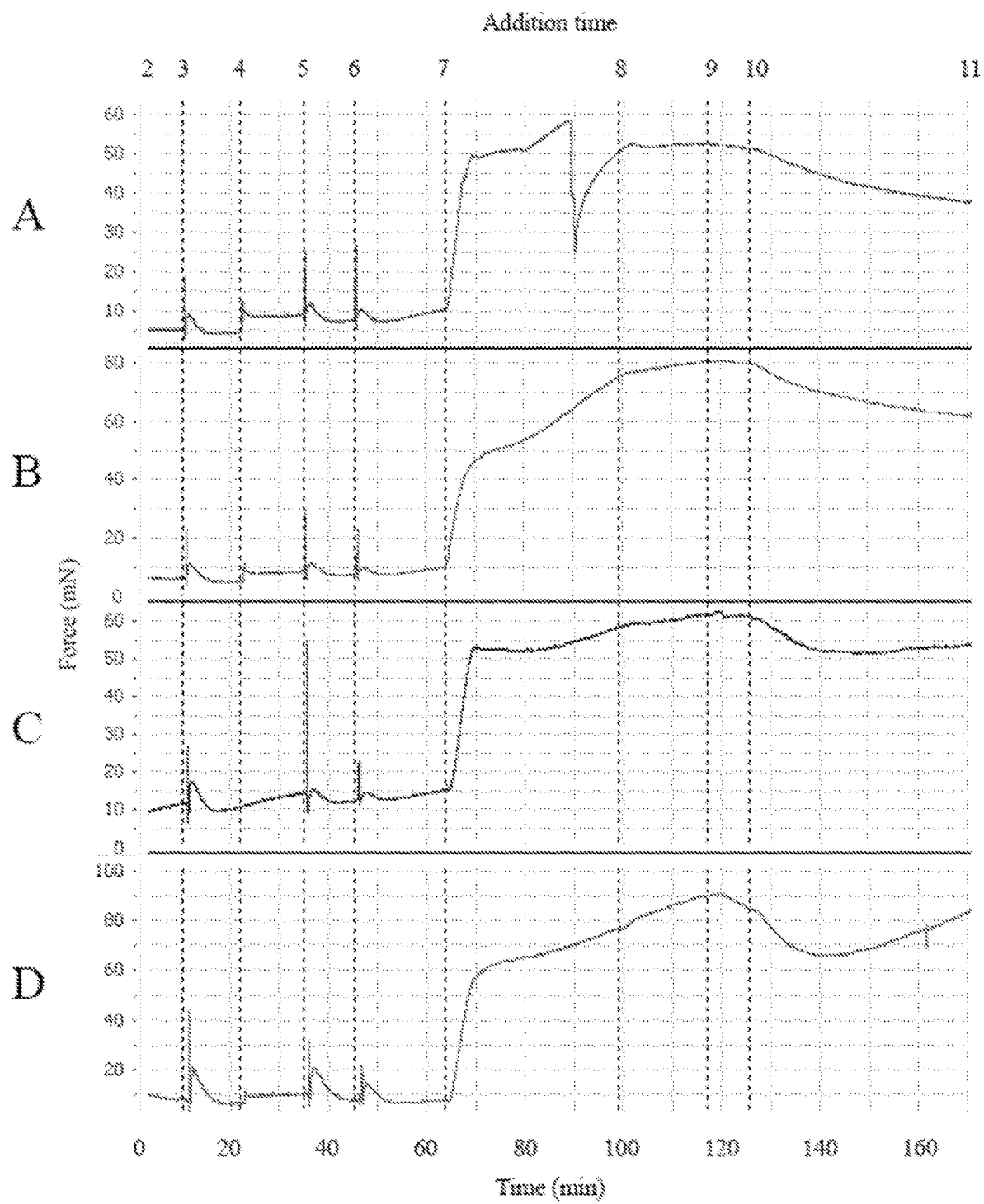
FIG. 1 shows the recorded contractions in four muscle strips in organ baths in Experiment I. All muscle strips are contracted by potassium at time 7. At time 8 the muscle strips are subjected to various doses of cnidimoside A, from top to bottom, subjected to the administration of 112, 38, 13 and 0 µM cnidimoside, the bottom strip being control. At time 9 0.4 µM adrenaline is added to all strips and at time 10 the adrenaline concentration in each bath is increased to 1.2 µM.

About 40 minutes after addition of potassium, cnidimoside A was given to the organ baths. Cnidimoside A was isolated from *Angelica archangelica* leaf by boiling the dried leaf in water, extracting the water phase by ethyl acetate and subjecting the resulting organic phase to silica acid chromatography column. Cnidimoside A is eluted by 10% methanol in chloroform after washing the column with ethyl acetate and chloroform. The cnidimoside A rich fractions were recrystallized in methanol. FIG. 1 shows the contraction in the four organ baths (A-D), in which the cnidimoside A dissolved in DMSO was added at time 8 is 112 μM (A), 38 μM (B) and 13 μM (C).

The muscle strip in the fourth organ bath (D in FIG. 1) received the same amount of DMSO but no cnidimoside A. About 20 and 30 minutes later (see FIG. 1, times 9 and 10) adrenaline was added to all organ baths, resulting in 0.4 (time 9) and 1.2 μM (time 10) final concentration, respectively. The control strip (D) reacted rapidly to the neurotransmitter by relaxing, but due to desensitization the relaxation is only temporary and after about 15 minutes the muscle starts contracting again, reaching the same level of contraction 50-60 minutes after the addition of cnidimoside A. On the other hand, the strips receiving cnidimoside A, react slower to this dose of adrenaline, but the desensitization is repressed dose-dependently. Desensitization occurred slowly in the presence of 13 μM cnidimoside A (C), and not observed at all in the presence of higher doses (A-B).

Experiment II

FIG. 2 shows the contraction-recordings of experiment II. About 75 minutes after addition of potassium, cnidimoside A dissolved in DMSO was added to three organ baths (E-G, time-10 in FIG. 2), the fourth receiving the same amount of DMSO (bottom graph (H) in FIG. 2). Fifteen minutes after the addition of cnidimoside A, adrenaline was added to all baths, to a final concentration of 2 μM (time 11 in FIG. 2). In the absence of cnidimoside A the muscle strip relaxed for about 15 minutes, but then started contracting again, reaching the same level of contraction about 50 minutes after the addition of adrenaline. In the presence of 200 μM cnidimoside A the desensitization occurs much slower, illustrating the desensitization effects of cnidimoside A.

Example 2

A Parallel, Randomised, Double-Blind, Placebo-Controlled Study to Investigate the Effect of Cnidimoside A on Frequent Urination and Overactive Bladder (OAB) in Men and Women Objective The primary study objective is to assess the effect of cnidimoside A compared with placebo, given twice daily, in reducing voiding frequency. Secondary objectives include investigating the effect of cnidimoside A on nocturia adjusted for sleep hours, number of daily voids adjusted for wake time and voids occurring shortly after the preceding void as well as overactive bladder symptoms according to the International OAB score (OABSS), quality of life according to ICIQ-OABqol and prostate symptoms for male participants according to the international prostate symptom score (IPSS). Follow up study will investigate maintenance of number of urinations in post-intervention.

Design

This is a parallel, randomised, double blind, placebo controlled study. Participants will make 4 visits to the study site over a period of up to 8 weeks. Screening for eligibility will take place at visits 1 and 2, among other based on study questionnaires (OABSS, ICIQ-OABqol and IPSS) and a 3-day voiding diary maintained by participants between those visits, starting Monday morning at Sam to Thursday morning at 8 am. Eligible participants will be randomised at visit 2 to receive cnidimoside A or placebo (1:1 in each gender group) for 6 weeks. Third visit will take place after approximately 6 weeks of cnidimoside A/placebo use. Participants will be asked to maintain a 3-day voiding diary in week 6 of the study, starting Monday morning at Sam to Thursday morning at Sam of that week, and symptoms will be assessed based on the study questionnaire (OABSS, ICIQ-OABqol and IPSS). Safety and tolerability will be assessed from reporting of adverse events, vital signs and urinalysis. Follow up will be at 3 weeks after last dose.

Study Population 100 male and 100 female participants, generally healthy and suspected or diagnosed with OAB that suffer from frequent urination will be enrolled into the study, 30-70 years of age with an average ≥1.5 nocturnal voids per night as determined by the participant diary during the screening period and/or less than 2 hours between voids at least half the time.

Study Product, Dose and Mode of Administration:

The participants receive two capsules daily, either containing 0.3 mg cnidimoside A in 100 mg extract (using water to extract) of *Angelica archangelica* leaf or a matching placebo.

Participants will be randomised to receive either cnidimoside A or matching placebo. Each gender group will be randomised to assuring equal partition in both. Participants will be instructed to take the study product twice daily, one in the morning and one in the evening before going to bed.

Duration of Study:

Duration of participation for each participant is approximately 10-11 weeks, including a 7-14 day screening period, 6 weeks of cnidimoside A/placebo use and a 3 week follow up.

Example 3

Toxicity Studies of Cnidimoside A

Experiment I

In a mouse experiment, we fed mice with about 77 mg *Angelica archangelica* water-extract (mixed in food) daily for 6 months. Assuming the mice to be on average 23 g and cnidimoside A content in the extract to be 0.15%, this means that the daily consumption of cnidimoside A was 3.35 mg/kg. No toxic effect was observed.

Experiment II

Further, a mouse experiment has been carried out with the mice receiving 100 mg/kg daily of cnidimoside A for 30 days, without affecting the weight of body, liver, spleen or thymus (Journal of Natural Chemistry, Vol. 62, No. 3, pp. 308-313).

The invention claimed is:

1. A method of treatment of a urinary condition in a human subject wherein the urinary condition is manifested by an overactive bladder, the method comprising administering to a human subject in need thereof a therapeutically effective dose of cnidimoside A.

2. The method of claim 1, wherein cnidimoside A is provided in a purified form.

3. The method of claim 1, wherein cnidimoside A is provided as a plant extract.

4. The method of claim 3, wherein the plant extract is from a plant from a genus selected from *Cnidium, Angelica* and *Corydalis*.

5. The method of claim 1, wherein the urinary condition is selected from overactive bladder, nocturia and urinary incontinence.

6. The method of claim 1, wherein the cnidimoside A is provided as a tablet or capsule for oral administration.

7. The method of claim 4, wherein the extract comprises in the range of 0.2 mg to 20 mg cnidimoside A per g of dry weight plant material.

* * * * *